United States Patent [19]
Tarvis

[11] Patent Number: 5,340,314
[45] Date of Patent: Aug. 23, 1994

[54] METHOD OF BONDING AND RELINING DENTURES

[76] Inventor: Jo-Ellen Tarvis, 80 Jamie La., Teaticket, Mass. 02536

[21] Appl. No.: 982,630

[22] Filed: Nov. 27, 1992

[51] Int. Cl.⁵ ............................................. A61C 13/02
[52] U.S. Cl. .................................................. 433/168.1
[58] Field of Search .................... 433/168.1, 169, 180, 433/199.1, 171

[56] References Cited

U.S. PATENT DOCUMENTS

| | | | |
|---|---|---|---|
| 1,050,561 | 1/1913 | Moore | 433/168.1 |
| 2,392,513 | 1/1946 | Town | 433/168.1 |
| 2,771,675 | 11/1956 | Willis | 433/168.1 |
| 2,897,593 | 8/1959 | Hollander et al. | 433/168.1 |
| 3,226,826 | 1/1966 | Town | 433/168.1 |
| 3,736,274 | 5/1973 | Schoenholz . | |
| 3,868,432 | 2/1975 | Keegan et al. . | |
| 3,878,135 | 4/1975 | Keegan et al. . | |
| 4,318,742 | 3/1982 | Lokken . | |

FOREIGN PATENT DOCUMENTS 902304  6/1972  Canada .

Primary Examiner—John G. Weiss
Assistant Examiner—Nicholas D. Lucchesi
Attorney, Agent, or Firm—Thomas A. Kahrl

[57] ABSTRACT

A method for holding a denture in place on a user's gum by applying dental wax in the cavity of a denture plate particularly a lower denture plate comprising the steps of providing a denture plate, providing dental wax, preparing a strip of dental wax, rolling the strip with the user's fingers, pressing the wax into the denture plate cavity placing the denture plate in the wearer's mouth on the lower gum in contact with the gum surface, biting down lightly on the denture and molding the wax with the residual heat of the mouth for completely providing a complete bond between the surface of the gum and the inner cavity of the denture plate.

4 Claims, 2 Drawing Sheets

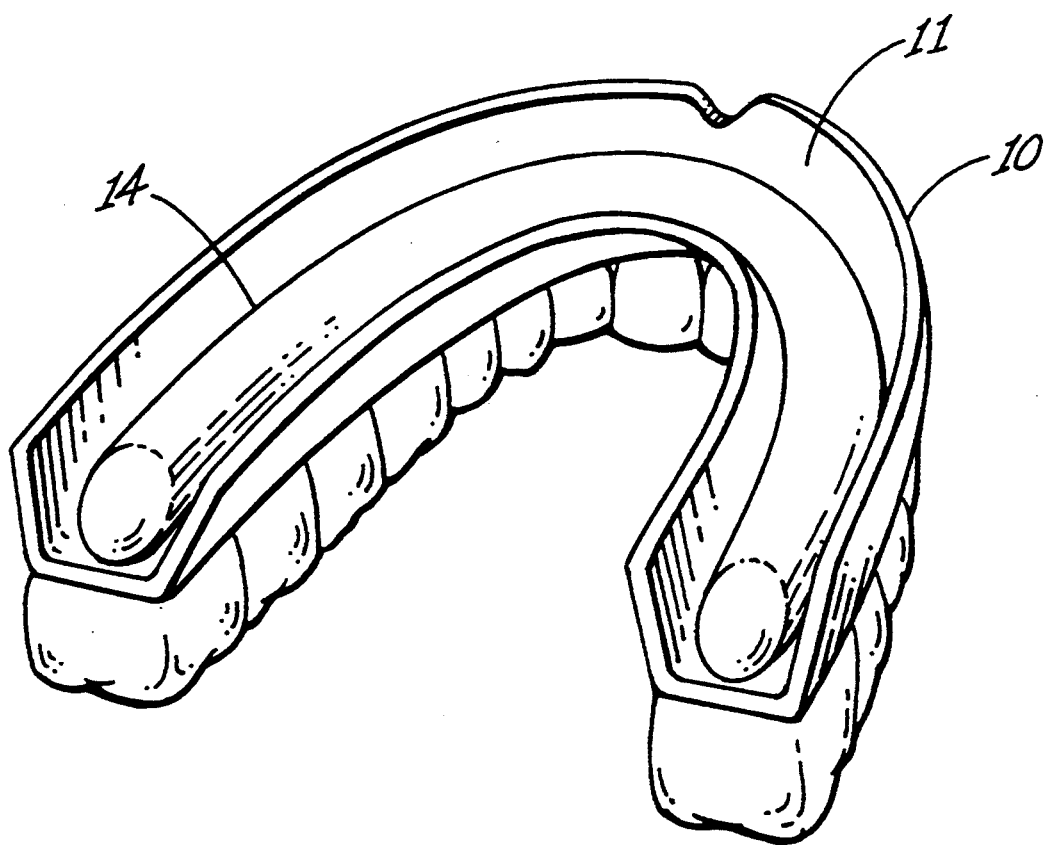
FIG_3

METHOD OF BONDING AND RELINING DENTURES

BACKGROUND OF THE INVENTION

I have discovered a new use for dental wax, commonly referred to as orthodontic wax. Dental wax is typically used for covering bands of orthodontic braces, and is sold over the counter under the "Hygienic" ® brand for multi ortho waxes or brand names such as "orthodontic wax." My new use for dental wax, is using dental wax as a means of adhering a dental denture to a wearer's gum.

Applicant is aware of prior art compounds for attaching dentures to gums, such as U.S. Pat. No. 4,318,742; Lokken, issued Mar. 9, 1982, U.S. Pat. No. 3,878,135; Keegan et al. issued on Apr. 15, 1975, U.S. Pat. No. 3,868,432, also Keegan et al., issued Feb. 25, 1975 and U.S. Pat. No. 3,736,274; Schoenholz issued May 29, 1973.

Lokken discloses an odontologic composition suited for use as a denture adhesive, the composition containing a major amount of gum base, wherein gum latex solids include natural gum solids such as Chicle, Chickle Gum, Zapota Gum and the like obtained from the sapodilla tree. Keegan et al., includes an anhydrous denture adhesive prepared to contain a mixture of cationic polymeric material and synthetic anionic gum material as an adhesive ingredient which may be formulated as a powder or anhydrous paste. Schoenholz is directed to a denture adhesive which comprises mallic anhydryde copolymer, a polymeric n-vinyl lactam and sodium carboxymyethylcellulous. Such prior art compounds are adapted for attaching dentures to gums and incorporate synthetic powdered material, typically composed of powders which must be mixed up to form a paste and applied to the dentures or are offered in paste-like form.

One of the functions served by the prior art compounds is to fill the gaps between the dentures and the wearer's gum to achieve a proper fit and to secure the dentures in the mouth. While dentures may be properly molded to provide a good fit when new, variations in a wearer's gum over a period of time typically produces gaps in the bonding surface between the denture and the gum. It is these gaps which interfere with the proper fit and makes for loose dentures which have a tendency to fall out much to the dissatisfaction of the wearer. An important function of the dentifrice compound is to provide a good fit and eliminate any gaps between the gum and the dentifrice as well as to provide a smooth comfortable fit with a minimum of discontinuities. Furthermore, prior art denture compounds tend to loosen due to the interaction with the saliva in the wearer's mouth producing new discontinuities and therefore become unsatisfactory over an extended period of usage.

The above noted disadvantages and drawbacks of the prior art methods and compounds are obviated by the present invention, which has for an object, the provision of a novel and improved method of bonding dentures to a wearer's gum which is extremely simple to practice, low in cost and reliable in operation over extended periods of time to the enhanced satisfaction of the user. Other features and advantages will herein after appear.

SUMMARY OF THE INVENTION

The present invention is directed to a method of bonding dentures to a wearer's gum, particularly the lower gum, to holding the denture in place in the wearer's oral cavity over an extended period of time, and to a method of relining dentures with dental wax.

In particular, the method of the invention is directed to a method of holding a denture in place on a user's gum, particularly the lower gum, comprising the steps of providing a denture plate for supplying substitute teeth, providing dental wax consisting of a paraffin base, commonly sold under the trade name of "Hygienic" Multi-Orthowax or as orthodontic wax, preparing a strip of dental wax by cutting, rolling the strip of the dental wax with a user's finger to extend the length of the strip to the length of the denture plate, pressing the strip of wax into the denture cavity such that the denture cavity is filled to a level no more than half-full, placing the denture plate in the wearer's oral cavity on a selected gum, biting down lightly on the denture; and molding the wax with the heat of the residual heat of the mouth to achieve a secure, comfortable fit.

In the preferred method, the strip of the dental wax is at least one and one-half inches in length and ⅜" inches in width. When the denture plate is pressed down against the user's gum, the wax contacts the gum surface of the wearer's gum, and, being heated spreads out to provide a complete contact surface with the wearers' gum immediately positioned within the denture cavity. After the denture has been molded in place by the action of the dental wax bonding to the surface of the wearer's gum, the denture and the gum have surfaces which are bonded together to provide a secure engagement for a period of not less than 10–16 hours of normal usage.

The method of the present invention also includes filling the spaces between the wearer's gum surface and the inner surface of the denture to insure a maximum surface for bonding the denture gum cavity to the surfaces of the wearer's gum to provide a lasting comfortable bond, and which does not irritate the wearer's gum.

A further feature of the dental wax is that upon removal of the denture from the wearer's gum and oral cavity, the dental wax can be removed from the denture plate by placing the denture in cold or ice water for a short period of time. By placing the denture in cold or ice water it causes the dental wax to harden, making it easy to remove to provide a clear surface on the denture for the next use.

In an alternate method a strip of dental wax may be applied to a denture, either an upper or lower denture, for relining. Where the strip of wax is provided to the user in strips, it may be used in a lower plate to provide a reline of the lower denture plate. Where the dental wax is provided as a flat surface, the wax may be easily fitted by the user under the upper plate for relining the upper plate.

The invention will be described for the purposes of illustration only in connection with certain embodiments; however, it is recognized that those persons skilled in the art may make various changes, modifications, improvements and additions on the illustrated embodiments all without departing from the spirit and scope of the invention.

BRIEF DESCRIPTION OF THE DRAWINGS

FIG. 3 is a schematic view of a denture plate with a gum cavity for accepting dental wax according to the present invention.

DESCRIPTION OF THE PREFERRED EMBODIMENT

Figure 1:
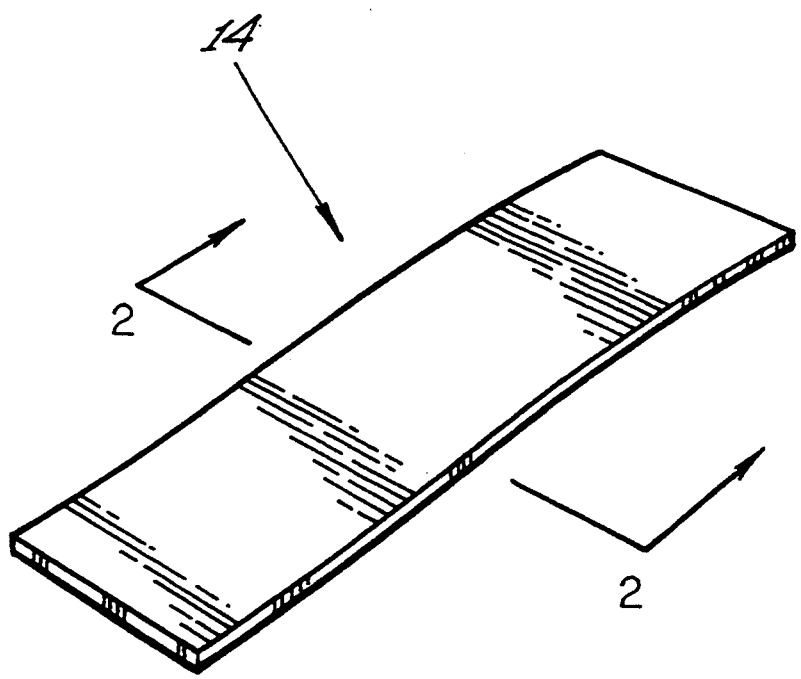
FIG. 1 is a perspective view of a strip of orthodontal wax employed in the present invention.
Figure 2:
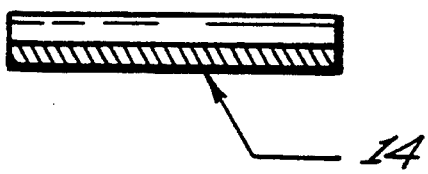
FIG. 2 is a cross section taken along line 2—2 of FIG. 1.

As is shown in the Figs., the invention is directed to a combination of a denture, denture wax and a wearer's gum for holding a denture in place on a user's gum comprising a denture plate 10 having a gum cavity 11 for supplying substitute teeth for a wearer and dental wax 14 for use as a bond for bonding the denture 10 to a wearer's gum, or alternatively as a reline of the denture plate 10.

The invention is further directed to a strip of dental wax 14 prepared by first cutting a strip and then rolling said strip with the wearer's fingers to extend the length of said strip 14 to the length of the denture plate 10, typically one and one-half inches in length and by pressing said strip 14 into the gum cavity 11 such that the gum cavity 11 is filled to a level of no more than half-full.

In the preferred embodiment, the denture plate 10 is then placed in a wearer's oral cavity and secured in place on a selected gum by the wearer by biting down lightly on the denture molding the strip of wax 14 with the residual heat of the wearer's oral cavity . Typically the strip of denture wax 14 is at least one and one-half inches in length and at least $\frac{3}{8}''$ inches in width for placement in the denture cavity 11.

In the preferred embodiment the denture plate 10 comprises a lower plate for use on a lower gum of a wearer.

What is claimed is:

1. A method for holding a denture in place on a wearer's gum comprising the steps of:
   a) providing a denture plate means for supplying substitute teeth comprising an elongated channel adapted to receive a wearer's gum, said channel being concave;
   b) providing orthodontal wax based on paraffin;
   c) preparing a strip of said wax;
   d) rolling the strip with the wearer's fingers to extend the length of the strip to the length of the denture plate;
   e) pressing the wax into the channel such that the channel is filled to a level of no more than half full;
   f) placing the denture plate means in the wearer's mouth;
   g) biting down lightly on the denture plate means; and
   h) molding the wax with the heat of the residual heat of the mouth, wherein a complete bond is established between the wearer's gum and the denture plate means.

2. The method of claim 1 wherein the strip is at least 1 and $\frac{1}{2}$ inches in length and $\frac{3}{8}$ inches in width.

3. The method of claim 1 wherein the denture plate means comprises a lower plate for use on a lower gum.

4. The method of claim 1 wherein the denture plate means comprises an upper plate for use on an upper gum.

* * * * *